United States Patent [19]

Clemence et al.

[11] Patent Number: 4,988,708

[45] Date of Patent: * Jan. 29, 1991

[54] ANALGESIC AND ANTI-INFLAMMATORY 4-OH QUINOLINE CARBOXYLIC ACID DERIVATIVES

[75] Inventors: François Clemence; Odile Le Martret, both of Paris; Françoisé Delevalleé, Fontenay-sous-Bois, all of France

[73] Assignee: Roussel Uclaf, Paris, France

[*] Notice: The portion of the term of this patent subsequent to Apr. 5, 2005 has been disclaimed.

[21] Appl. No.: 183,911

[22] Filed: Apr. 20, 1988

Related U.S. Application Data

[63] Continuation-in-part of Ser. No. 30,680, Mar. 24, 1987, Pat. No. 4,845,105, which is a continuation-in-part of Ser. No. 831,356, Feb. 20, 1986, abandoned, which is a continuation-in-part of Ser. No. 790,064, Oct. 22, 1985, Pat. No. 4,735,951.

[30] Foreign Application Priority Data

Oct. 30, 1984 [FR] France .................. 8416573
Jul. 25, 1985 [FR] France .................. 8511389

[51] Int. Cl.$^5$ .......... A61K 31/47; C07D 417/14; C07D 401/14; C07D 413/14
[52] U.S. Cl. ..................... 514/312; 514/256; 544/322; 546/156
[58] Field of Search ......... 546/156; 514/312, 256; 544/372

[56] References Cited

U.S. PATENT DOCUMENTS 4,486,438 12/1984 Clémence et al. ........ 546/156 X
4,735,951 5/1988 Cléence et al. .......... 514/312
4,845,105 7/1989 Clémence et al. ........ 514/312

FOREIGN PATENT DOCUMENTS 0214004 3/1987 European Pat. Off. .
2551437 3/1985 France .
2572404 5/1986 France .

Primary Examiner—Diana Rivers
Attorney, Agent, or Firm—Bierman and Muserlian

[57] ABSTRACT

A compound selected from the group consisting of optical isomers and racemates of 4-hydroxy-3-quinoline carboxylates of the formula

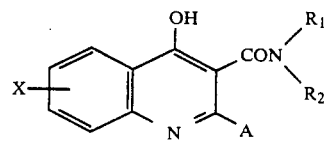

wherein X is in the 5-, 6-, 7- or 8-position and is selected from the group consisting of hydrogen, halogen, alkyl of 1 to 5 carbon atoms, alkoxy of 1 to 4 carbon atoms, —CF$_3$, —SCF$_3$, and OCF$_3$, R$_1$ is selected from the group consisting of hydrogen and alkyl of 1 to 4 carbon atoms, R$_2$ is selected from the group consisting of thiazolyl, 4,5-dihydrothiazolyl, pyridinyl, oxazolyl, isoxazolyl, imidazolyl, pyrimidyl and tetrazolyl, all optionally substituted with alkyl of 1 to 4 carbon atoms and phenyl and phenyl substituted with at least one member of the group consisting of —OH, alkyl and alkoxy of 1 to 4 carbon atoms, —CF$_3$, —NO$_2$ and halogen, A is

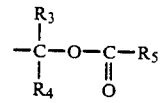

in which R$_3$ and R$_4$ are individually selected from the group consisting of hydrogen, alkyl of 1 to 4 carbon atoms and aryl, R$_5$ is heteroaryl f 3 to 14 carbon atoms optionally substituted with alkyl of 1 to 4 carbon atoms and their non-toxic, pharmaceutically acceptable salts with acids or bases having analgesic and anti-inflammatory activity.

36 Claims, No Drawings

ANALGESIC AND ANTI-INFLAMMATORY 4-OH QUINOLINE CARBOXYLIC ACID DERIVATIVES

PRIOR APPLICATION

This application is a continuation-in-part of U.S. patent application Ser. No. 030,680 filed Mar. 24, 1987, now U.S. Pat. No. 4,845,105, which is a continuation-in-part of U.S. patent application Serial No. 831,356 filed Feb. 20, 1986, now abandoned, which is a continuation-in-part of U.S. patent application Ser. No.790,064 filed Oct. 22, 1985, now U.S. Pat. No. 4,735,951.

STATE OF THE ART

U.S. Pat. No. 4,486,438 describes 4-hydroxy-3-quinoline carboxylic acid derivatives and in particular racemic 4-hydroxy2-1-hydroxypropyl) N-(2-thiazolyl)-8-trifluoromethyl-3-quinolinecarboxamide as having analgesic activity.

OBJECTS OF THE INVENTION

It is an object of the invention to provide the novel compounds of formula I and their salts with acids and bases.

It is another object of the invention to provide novel analgesic and anti-inflammatory compositions and a novel method of relieving pain and inflammation in warm-blooded animals. These and other objects and advantages of the invention will become obvious from the following detailed description.

THE INVENTION

The novel compounds of the invention are selected from the group consisting of a compound of the formula

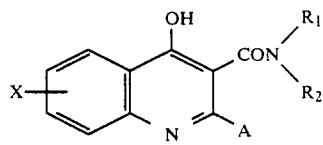

wherein X is in the 5-, 6-, 7- or 8-position and is selected from the group consisting of hydrogen, halogen, alkyl of 1 to 5 carbon atoms, alkoxy of 1 to 4 carbon atoms, $-CF_3$, $-SCF_3$ and $OCF_3$, $R_1$ is selected from the group consisting of hydrogen and alkyl of 1 to 4 carbon atoms, $R_2$ is selected from the group consisting of thiazolyl, 4,5-dihydrothiazolyl, pyridinyl, oxazolyl, isoxazolyl, imidazolyl, pyrimidyl and tetrazolyl all optionally substituted with alkyl of 1 to 4 carbon atoms and phenyl and phenyl substituted with at least one member of the group consisting of -OH, alkyl and alkoxy of 1 to 4 carbon atoms, $-CF_3$, $-NO_2$ and halogen, A is

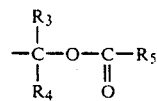

in which $R_3$ and $R_4$ are individually selected from the group consisting of hydrogen, alkyl of 1 to 4 carbon atoms and aryl, $R_5$ is heteroaryl of 3 to 14 carbon atoms optionally substituted with alkyl of 1 to 4 carbon atoms and their non-toxic, pharmaceutically acceptable salts with acids and bases.

Examples of X are halogens such as chlorine, alkyl such as methyl, ethyl, n-propyl, isopropyl, n-butyl, isobutyl and n-pentyl and alkoxy such as methoxy, ethoxy and n-propoxy.

When $R_1$ is alkyl, it is preferably methyl or ethyl.

When $R_2$ is a heterocyclic substituted with alkyl, the alkyl is preferably methyl or ethyl. When $R_2$ is substituted phenyl, the substituent is preferably at least one member of the group consisting of —OH, methyl, ethyl, methoxy, ethoxy, $-CF_3$, $-NO_2$ and chloride.

When $R_3$ is alkyl, it is preferably methyl, ethyl, propyl, isopropyl, butyl or isobutyl. When $R_3$ is aryl, it is preferably phenyl or naphthyl.

When $R_4$ is alkyl, it is preferably methyl, ethyl, propyl, isopropyl, butyl or isobutyl When $R_4$ is aryl, it is preferably phenyl or naphthyl.

$R_5$ is heteroaryl and it is preferably a pyridyl, indolyl, thienyl, oxazolyl, thiazolyl, pyrimidyl, benzo [b] thienyl and benzothiazolyl, optionally substituted with alkyl of 1 to 5 carbon atoms.

Examples of suitable bases for the salts are alkali metals such as sodium or potassium and amines such as trimethylamine or dimethylamine.

Examples of suitable acids for the acid addition salts are mineral acids such as hydrochloric acid, hydrobromic acid, sulfuric acid and phosphoric acid, as well as sulfonic acids such as the alkyl or arylsulfonic acids, for example, methanesulfonic or p-toluene sulfonic acid.

Among the preferred compounds of the invention are those of formula I wherein X is in the 8-position, especially when X is $-CF_3$, those wherein X is chlorine in the 7-position, those wherein $R_2$ is thiazolyl, those wherein $R_3$ is hydrogen, those wherein $R_4$ is ethyl, those wherein $R_5$ is indolyl, those wherein $R_5$ is thiazolyl optionally substituted with alkyl of 1 to 5 carbon atoms, those wherein $R_1$ is hydrogen and their non-toxic, pharmaceutically acceptable salts with acids and bases.

Specific preferred compounds of formula I are 1-[4-hydroxy -3-{[(2-aminothiazolyl)-carbonyl]-8-trifluoromethyl-2-quinolinyl}-propyl]1H-indole-carboxylate and 1-[4-hydroxy-3-{[(2-thiazolyl)-amino]-carboxyl}-8-trifluoromethyl-2-quinolinyl -propyl]2-propyl-5-thiazole-carboxylate in racemic or optically active form and their salts with acids and bases.

The novel process of the invention for the preparation of compounds of formula I comprises reacting a compound of the formula

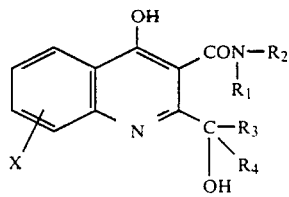

wherein X, $R_1$, $R_2$, $R_3$ and $R_4$ are defined as above with an acid of the formula

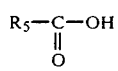

to obtain the corresponding compound of formula I which, if desired, is submitted to the action of an acid to form its acid addition salt.

In a preferred mode of the process, the reaction is effected in the presence of dicyclohexyl-carbodiimide and 4-dimethylamino-pyridine in an organic solvent and when $R_5$ is alkyl substituted by amino, an acid is used in which the amino is blocked and the freeing of the amino after esterification is effected by action of an acid. When it is desired to prepare an optically active product of formula I, there is used at the start an alcohol which is first resolved by the intermediary of an optically active acid leading to a mixture of esters which are separated by usual methods such as by crystallization or chromatography.

The products of formula II are described in European Patent Application No. 84-402074.3 published under number 141713.

In a modification of the process of the invention for compounds of formula I wherein $R_1$ is hydrogen, a compound of the formula

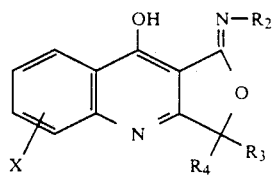

wherein X, $R_2$, $R_3$ and $R_4$ are defined as above is reacted with an acid of the formula $R_5$—COOH to obtain a compound of formula I which, if desired, is submitted to the action of an acid to form its acid addition salt.

The compounds of formula III correspond to products of formula XII claimed in the Belgian Patent No. 896,941 and they can be prepared by the process described in that patent. They can also be prepared by the process described in the European Application No. 141,713 illustrated as follows:

In the products of formulae A,B,C,D and III, X, $R_2$, $R_3$ and $R_4$ have the above definitions, X' is halogen and R is alkyl of 1 to 8 carbon atoms.

In a preferred mode of the process of the invention, the reaction between the compound of formula III and the acid $R_5$COOH is carried out at a temperature between 100° and 150° C., or if the case arises, at reflux of the acid.

The process of the invention for the preparation of the compounds of Formula I comprises reacting a compound of the formula.

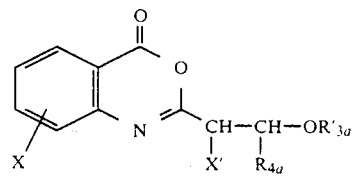

wherein X and $R_{4a}$ have the above definitions, $R'_{3a}$ is alkyl of 1 to 4 carbon atoms or aryl and X' is halogen either with a compound of the formula

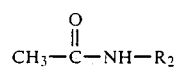

wherein $R_2$ has the above definition to obtain a compound of the formula

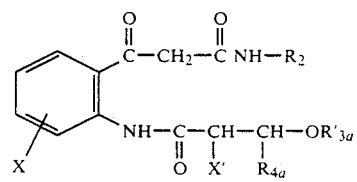

or in the presence of a base with a compound of the formula

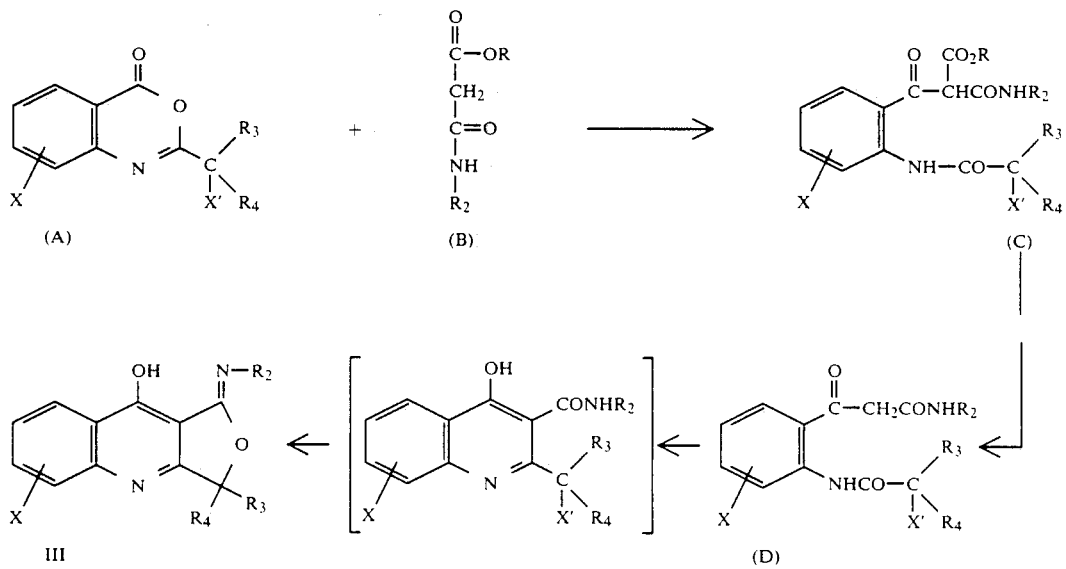

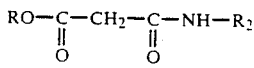

$III_B$ wherein $R_2$ has the above definition and R is alkyl of 1 to 8 carbon atoms to obtain a compound of the formula

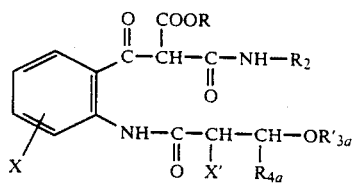

A which is decarbalkoxylated to obtain a compound of Formula IV, cyclizing the latter in the presence of an alkaline agent to obtain a compound of the formula

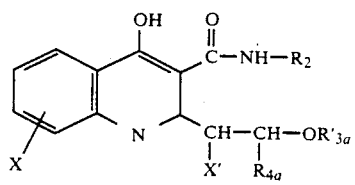

V which is transformed into a compound of the formula

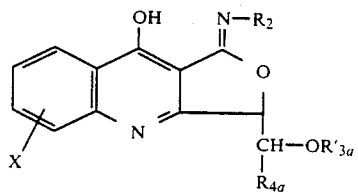

VI and treating the latter either with an acid of the formula $R_{5\text{-}a}$ COOH wherein $R_{5a}$ has the above definition to obtain a compound of Formula I wherein X, $R_2$ and $R_{4a}$ have the above definitions, $R_{2a}$ is

and $R_{3a}$ is alkyl of 1 to 4 carbon atoms or aryl or with an acid hydrolysis agent to obtain a compound of Formula I wherein X, $R_2$ and $R_{4a}$ have the above definitions, $R_{2a}$ is hydrogen and $R_{3a}$ is alkyl of 1 to 4 carbon atoms or aryl which can be optionally transformed into a compound of Formula 1 wherein X, $R_2$ and $R_{4a}$ have the above definitions and either one or both of the hydroxyls may be esterified or etherified to obtain a compound of formula I wherein $R_{2a}$ and/or $R_{3a}$ are individually alkyl of 1 to 4 carbon atoms or aryl or

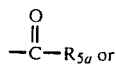

treating the compound of Formula I where $R_{2a}$ and $R_{3a}$ are hydrogen with acetone in the presence of an acid agent to obtain the corresponding acetonide. The compounds of Formula I may be reacted with an acid or base to form the corresponding salt.

In a preferred mode of the process, X' is chlorine and the reaction of the compounds of Formulae 11' and $111_A$ is effected in the presence of an organolithium or a lithium amide for example butyllithium or lithium diisopropylamide at a low temperature on the order of −70° C.

The reaction of compounds of Formulae II' and $III_B$ is effected in the presence of a base such as sodium hydroxide and the reaction is effected at room temperature. The decarbalkoxylation reaction may be effected as described in European patent No. 141,713

The cyclization of the compounds of Formula IV is effected in the presence of an alkaline agent such as alkali metal hydride or carbonate or an amine, for example in the presence of sodium hydride, sodium carbonate, potassium carbonate, piperidine, 4-aminopyridine, 4-dimethylamino-pyridine, triethylamine, 1,5-diazabicyclo[4,3,0]non-5-ene, 1,4-diazabicyclo[2,2,2]octane or 1,5-diazabicyclo[5,4,0]undec-5-ene. The cyclization is effected in a solvent, preferably tetrahydrofuran, but other solvents such as dimethylformamide, benzene or toluene may be used.

The acid hydrolysis of the compounds of Formula VI is preferably effected with hydrochloric acid but other acids such as sulfuric acid may be used. The transformation of a compound of Formula 1 wherein $R_{3a}$ is alkyl of 1 to 4 carbon atoms or aryl into a compound wherein $R_{3a}$ is hydrogen is effected in the presence of trimethylsilane iodide or boron tribromide in a solvent such as acetonitrile or methylene chloride.

The esterification or etherification of one or two of the hydroxyls of Formula 1 may be effected by the known methods. The acid agent for the acetonide formation may be p-toluene sulfonic acid, for example.

Another process for the preparation of a compound of Formula I comprises reacting a compound of the formula

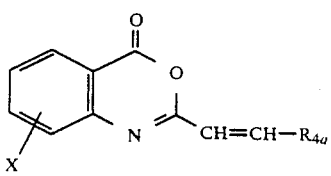

$II_A$ wherein $R_{4a}$ has the above definition with a compound of Formula $III_A$ wherein $R_2$ has the above definition to form a compound of the formula

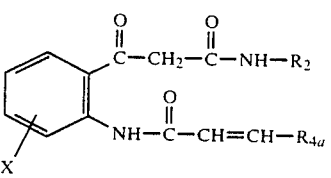

$IV_A$ and cyclizing the latter in the presence of an alkaline agent to obtain a compound of the formula

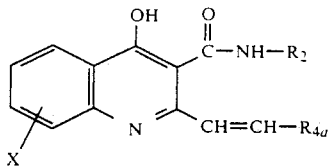

which can be transformed into the compound of Formula I wherein X, $R_2$ and $R_{4a}$ have the above definitions and $R_{2a}$ and $R_{3a}$ are hydrogen and the latter may be esterified or etherified to obtain the compound of Formula I wherein $R_{2a}$ and/or $R_{3a}$ are alkyl of 1 to 4 carbon atoms,

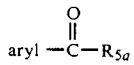

or the compounds of Formula I wherein $R_{2a}$ and $R_{3a}$ are hydrogen may be reacted with acetone in the presence of an acid agent to obtain the corresponding acetonide and the compounds of Formula I may be reacted with a base or acid to obtain the corresponding salt.

The passage of the compound of Formula $II_A$ to the compound of Formula $IV_A$ and the cyclization to form the compound of Formula $V_A$ may be effected as discussed above. The transformation of the compound of Formula $V_A$ into the corresponding dihydroxy compound may be effected with potassium permanganate in the presence of triethyl benzyl ammonium chloride. The etherification and esterification may be effected by known methods and the acid agent or the acetonide formation may be p-toluene sulfonic acid. The novel analgesic and anti-inflammatory compositions of the invention are comprised of an analgesically and anti-inflammatorily effective amount of at least one member of the group consisting of a compound of Formula I and its non-toxic pharmaceutically acceptable acid addition salts and an inert pharmaceutical carrier or excipient.

The novel analgesic and anti-inflammatory compositions of the invention are also comprised of an analgesically and antiinflammatorily effective amount of at least one member of the group consisting of 1-[4-hydroxy -3-{[(2-aminothiazolyl)-carbonyl]-8-trifluoromethyl-2-quinolinyl}-propyl]1H-indole-carboxylate and 1-[4-hydroxy-3-{[(2-thiazolyl)-amino]-carboxyl]-8-trifluoromethyl-2-quinolinyl -propy[2-propyl-5-thiazole-carboxylate in racemic or optically active form and their non-toxic pharmaceutically acceptable acid addition salts and an inert pharmaceutical carrier or excipient.

The compositions may be in the form of tablets, dragees, gelules, granules, suppositories, injectable solutions or suspensions, pomades, creams, gels and aerosol preparations formed in the usual fashion.

Examples of suitable excipients are talc, arabic gum, lactose, starch, magnesium stearate, cacao butter, aqueous and non-aqueous vehicles, fatty bodies of animal or vegetable origin, paraffinic derivatives, glycols, diverse wetting agents, dispersants and emulsifiers and perservatives.

The compositions due to their analgesic and very active anti-inflammatory activity are useful for the treatment of muscular, articular or nervous pain, dental pain, rhumatismatic affections, zona, and migraines as well as a complementary treatment (or infections and feverish states.

The compositions are also useful for the treatment of degenerative inflammatory maladies such as osteoarthrosis, various collagen diseases (tendinitis, etc.), rheumatic maladies (rheumatoid polyarthritis, ankylosing spondylarthritis), as well as the treatment of other maladies of auto-immune nature such as disseminated erythematous lupus glomerulonephritis, multiple sclerosis.

The novel method of the invention for relieving pain and inflammation in warm-blooded animals, including humans, comprises administering to warm-blooded animals an analgesically and anti-inflammatorily effective amount of at least one compound selected from the group consisting of a compound of Formula I and its non toxic, pharmaceutically acceptable slats.

The novel method of the invention for relieving pain and inflammation in warm-blooded animals, including humans, comprises administering to warm-blooded animals an analgesically and antiinflammatorily effective amount of at least one member of the group consisting of 1-[4-hydroxy -3-{[(2-aminothiazolyl)-carbonyl]-8-tri(uoromethyl-2-quinolinyl -propyl]1H-indole-carboxylate and 1-[4-hydroxy-3-}[(2-thiazolyl)-amino]-carboxyl}-8-trifluoromethyl-2-quinolinyl -propyl 2-propyl-5-thiazole-carboxylate in racemic or optically active form and their non-toxic, pharmaceutically acceptable salts.

The said carboxamides may be prepared by the process described in U.S. Pat. No. 4,486,438.

The compounds may be administered orally, rectally, parenterally or topically to the skin or mucous. The usual effective dose is dependent on the specific compound and the method of administration, and the conditions treated and may be 0.25 to 25 mg/kg per day in the adult by oral route.

In the following examples there are described several preferred embodiments to illustrate the invention. However, it should be understood that the invention is not intended to be limited to the specific embodiments.

EXAMPLE 1

4-hydroxy-2-methoxy-ethyl)-N-(2-thiazolyl)-8-(trifluoromethyl)-3-quinoline carboxamide

Step A:

2-[(2-chloro-3-methoxy-1-oxopropyl)amino]β-oxo-N-(2-thiazolyl)-3-trifluoromethyl benzene propanamide 350 ml of a solution of n-butyl lithium in hexane were added at 0° C. to a suspension of 34 g of 2-acetylamino thiazole in 1100 ml of tetrahydrofuran and after cooling the mixture to −70° to −75° C., a solution of 36.78g of 2-(1-chloro-2-methoxyethyl)-8-trifluoromethyl-4-H-3,1,-benzoxazine-4-one [prepared in Step A of Example 12 of European patent No. 40,573 from 2-chloro-3-methoxy propanoic acid (Chem. Ber., Volume 92, Page 1081-1087, 1959) and 2-amino-3-trifluoromethyl benzoic acid] in 250 ml of tetrahydrofuran was added thereto. The solution was poured into aqueous hydrochloric acid and the mixture was extracted with ether. The organic phase was washed with N hydrochloric acid with water, was dried and evaporated to dryness under reduced pressure. The residue was empasted with ether, vacuum filtered, washed with ether and dried under reduced pressure to obtain 33.35g of 2-[(2-chloro-3-methoxy-1-oxopropyl)amino]β-oxo-N (2-thiazolyl)-3-(trifluoromethyl)-benzene propanamide melting at 190° C.

Analysis: $C_{17}H_{15}N_3O_4F_3SCl$; molecular weight = 449.845.

|  | % C | % H | % N | % F | % Cl | % S |
|---|---|---|---|---|---|---|
| Calculated: | 45.39 | 3.36 | 9.34 | 12.67 | 7.88 | 7.13 |
| Found: | 45.6 | 3.4 | 9.0 | 12.4 | 7.8 | 7.1 |

Step B:
2-(1-chloro-2-methoxyethyl)-4-hydroxy-N-(2-thiazolyl)-8-trifluoromethyl-3-quinoline carboxamide A mixture of 33.35g of the product of Step A, 10g of 4-dimethylamino-pyridine and 300ml of tetrahydrofuran was refluxed for 30 minutes and was then cooled to room temperature and poured into a mixture of water and 2N hydrochloric acid. The mixture was extracted with ethyl acetate and the organic phase was washed, dried and evaporated to dryness. The residue was empasted with ether, vacuum filtered, washed and dried under reduced presssure at 60° C. to obtain 28.2g of 2-(1-chloro-2-methoxyethyl)-4-hydroxy-N-(2-thiazolyl)-8-trifluoromethyl-3-quinoline carboxamide melting at 186° C.

Step C:
1,3-dihydro-3-(methoxymethyl)-1-[(2-thiazolyl)-iminol]-5-trifluoromethylfuro[3,4,b]quinolin-9-ol A mixture of 23.9g of the product of Step B, 7.7g of potassium tertbutylate and 550ml of dioxane was refluxed for 30 minutes and the dioxane was evaporated under reduced pressure. The residue was taken up in a mixture of water and 2N hydrochloric acid and the insoluble matter was extracted with an 8-1 ethyl acetate-tetrahydrofuran mixture. The organic phase was washed with water and the combined aqueous phase was neutralized with a saturated aqueous sodium bicarbonate solution. The mixture was extracted with ethyl acetate and the organic phase was washed with water, dried and evaporated to dryness under reduced pressure to obtain 22g of 1,3-dihydro-3-(methoxymethyl)-1-[(2-thiazolyl)-iminol]-5-trifluoromethylfuro [3,4,b]quinolin-9-ol.

Step D:
4-hydroxy-2-(1-hydroxy-2-methoxyethyl)-N-(2-thiazolyl)-8-(trifluoromethyl)-3-quinoline carboxamide A solution of 22g of the product of Step C, 70ml of water and 30ml of concentrated hydrochloric acid was stirred at room temperature for 16 hours and was vacuum filtered. The product was washed with water and was taken up in 200ml of water. The mixture was extracted with a 1-1 mixture of ethyl acetate and tetrahydrofuran and the organic phase was washed with water, dried and evaporated to dryness under reduced pressure to obtain 15g of residue. The latter was chromatographed over silica and eluted with ethyl acetate to obtain 12.5g of product which was triturated in ether, vacuum filtered and dried under reduced pressure at 100° C. to obtain 11.83g of 4-hydroxy-2-(1-hydroxy-2-methoxy-ethyl)-N-(2-thiazolyl)-8-(trifluoromethyl)-3-quinoline carboxamide melting at 216°-218° C.

Analysis: $C_{17}H_{14}O_4N_3F_3S$; molecular weight = 413.384

|  | % C | % H | % N | % F | % S |
|---|---|---|---|---|---|
| Calculated: | 49.39 | 3.41 | 10.16 | 13.76 | 7.76 |
| Found: | 49.5 | 3.4 | 10.2 | 13.9 | 7.7 |

EXAMPLE 2
2-(1,2-dihydroxyethyl)-4-hydroxy-N-(2-thiazolyl)-8-trifluoromethy-3-quinoline carboxamide 6.7ml of trimethylsilane iodide were slowly added under an inert atmosphere to a mixture of 6.5g of the product of Example 1 and 120ml of acetonitrile and the mixture was stirred at room temperature for 16 hours and was poured into 400ml of water and 50ml of sodium bisulphate. The suspension was stirred at room temperature for 45 minutes and 100ml of ether were added followed by stirring for 30 minutes. The mixture was vacuum filtered and the product was washed with water and dried under reduced pressure at 75° C. for 16 hours to obtain 5.9g of product which was dissolved in 75 ml of dimethylformamide. The solution was filtered and ether was added to the filtrate. The mixture was iced and vacuum filtered and the product was washed with ether and dried under reduced pressure at 120° C. to obtain 4.86 of 2-(1,2-dihydroxyethyl)-4-hydroxy-N-(2-thiazolyl)-8-trifluoromethyl-3-quinoline carboxamide melting at 255° C.

Analysis: $C_{16}H_{12}N_3F_3O_4S$; molecular weight = 399.356

|  | % C | % H | % N | % F | % S |
|---|---|---|---|---|---|
| Calculated: | 48.12 | 3.03 | 10.52 | 14.27 | 8.03 |
| Found: | 48.0 | 3.0 | 10.4 | 14.1 | 8.0 |

EXAMPLE 3
2-(1,2-dihydroxypropyl)-4-hydroxy-N-(2-thiazolyl)-8-trifluoromethyl-3-quinoline carboxamide

Step A:
β-oxo-2-[(1-oxo-2-butenyl)-amino[-N-(2-thiazolyl)-3-trifluoromethyl-benzene-proponamide Using the procedure of Step A of Example 1, 19.44 g of 2-acetylamino thiazole and 17.3g of 2-(1-propenyl)-8-trifluoromethyl-4H-3,1-benzoxazin-4-one [prepared by Step A of Example 12 of European patent No. 40,573 from crotonyl chloride and 2-amino-trifluoromethyl benzoic acid] were reacted to obtain 19.03g of β-oxo-2-[(1-oxo-2-butenyl)-amino]-N-(2-thiazolyl)-3-trifluoromethyl-benzene-proponamide melting at 206°-208° C.

Step B:
4-hydroxy-2-(1-propenyl)-N-(2-thiazolyl)-8-trifluoromethyl-3-quinoline-carboxamide 17.5g of the product of Step A were added to a solution of 175ml of dimethylacetamide and a mixture of 2.11 g of sodium hydride as a 50% dispersion in oil and 100 ml of dimethylacetamide and the mixture was heated at 120° C. for 30 minutes and was then cooled. The mixture was poured into a mixture of water and 2N hydrochloric acid and the mixture was vacuum filtered. The product was washed with water and dried under pressure at 80° C. to obtain 16.7g of 4-hydroxy-2-(1- propenyl)-N-(2-thiazolyl)-8-trifluoromethyl-3-quinoline-carboxamide melting at 265° C.

Step C:
2-(1,2-dihydroxypropyl)-4-hydroxy-N-(2-thiazolyl)-8-trifluoromethyl-3-quinoline carboxamide A mixture of 12.2g of the product of Step B, 300ml of methylene chloride, 9.16g of methylbenzyl ammonium chloride and 6.32 g of potassium permanganate was stirred at 0° C. for one hour and then 150 ml of iced water were added followed by the addition of 150 ml of sodium bisulfite solution. The mixture was vacuum filtered and the product was washed with water and partially dissolved in tetrahydrofuran. The organic solution was dried and concentrated to dryness under reduced pressure to obtain 5.8 g of residue. The latter was dissolved in luke warm dimethylformamide and the solution was filtered. The filtrate was concentrated to about 40 ml and 60 ml of ether were added thereto. The iced mixture was vacuum filtered and the product was washed with ether and dried under reduced pressure at 100° C. The product was dissolved in tetrahydrofuran and the solution was filtered and evaporated to dryness under reduced pressure. The residue was triturated with ethyl acetate and was vacuum filtered. The product was washed and was dried under reduced pressure at 100° C. to obtain 3.04g of 2-(1,2-dihydroxypropyl)-4-hydroxy-N-(2-thiazolyl)-8-trifluoromethyl-3-quinoline carboxamide melting at 275° C.

Analysis: $C_{17}H_{14}N_3O_4F_3S$; molecular weight=413.384.

|  | % C | % H | % N | % F | % S |
|---|---|---|---|---|---|
| Calculated: | 49.39 | 3.41 | 10.16 | 13.79 | 7.76 |
| Found: | 49.3 | 3.3 | 10.1 | 14.1 | 7.8 |

EXAMPLE 4

2-(1,2-bis-(1-oxopropoxy)-ethyl-4-hydroxy-N-(2-thiazolyl)-8-trifluoromethyl-3-quinoline-carboxamide 2.9 g of dicyclohexylcarbodiimide were added over 5 minutes at 20° C. to a mixture of 2.15g of the product of Example 2, 70 ml of methylene chloride and 0.96 ml of propionic acid and then 2.4 g of 4-dimethylamino-pyridine were added. The mixture was stirred for 90 minutes and was filtered. The filtrate was washed with a saturated aqueous sodium carbonate solution, with aqueous hydrochloric acid, then with water, was dried and evaporated to dryness. The residue was crystallized from acetonitrile to obtain 1.34 g of 2-[1,2-bis-(1-oxopropoxy)ethyl]-4-hydroxy-N-(2-thiazolyl)-8-trifluoromethyl-3-quinolinecarboxamide melting at 206° C.

Analysis: $C_{22}H_{20}F_3N_3O_6S$; molecular weight=511.479.

|  | % C | % H | % N | % S | % F |
|---|---|---|---|---|---|
| Calculated: | 51.66 | 3.94 | 8.22 | 6.27 | 11.14 |
| Found: | 51.7 | 3.9 | 8.1 | 6.2 | 11.1 |

EXAMPLE 5

2-[2-methoxy-1-(1-oxopropoxy)-ethyl]-4-hydroxy-N-(2-thiazolyl)-8-trifluoromethyl-3-quinoline carboxamide Using the procedure of Example 4, 2 g of the product of Example 1, 0.4 ml of propionic acid, 1.2 g of dicyclohexylcarbodiimide and 0.3 g of 4-dimethylamino-pyridine were reacted to obtain 1 g of 2,[2-methoxy-1-(1-oxopropoxy)-ethyl]-4-hydroxy-N-(2-thiazolyl)-8-trifluoromethyl-3-quinoline carboxamide melting at 190° C.

Analysis: $C_{20}H_{18}F_3N_3O_5S$; molecular weight=469.442.

|  | % C | % H | % F | % N | % S |
|---|---|---|---|---|---|
| Calculated: | 51.17 | 3.87 | 12.14 | 8.95 | 6.83 |
| Found: | 51.5 | 4.0 | 11.9 | 8.9 | 6.5 |

EXAMPLE 6

2-[1,2-dibenzoyloxy ethyl]-4-hydroxy-N-(2-thiazolyl)-8-trifluoromethyl-3-quinoline-carboxamide Using the procedure of Example 4, 0.5 g of the product of Example 2, 0.37 g of benzoic acid, 0.67 g of dicyclohexylcarbodiimide and 0.075 g of 4-dimethylamino-pyridin were reacted to obtain 0.8 g of raw product. The latter was dissolved in 15 ml of tetrahydrofuran and 0.3 ml of a 5.7 N solution of hydrochloric acid in ethanol were added. The mixture was vacuum filtered and the crystals were dissolved in a water-ethyl acetate mixture. The solution was extracted with ethyl acetate and the organic phase was dried and evaporated to dryness. The residue was dissolved in tetrahydrofuran and ethyl was added. The mixture was cooled to 0° C. for 2 hours and was vacuum filtered. The crystals were dried to obtain 0.33 g of 2-[1,2-dibenzoyloxy ethyl]-4-hydroxy-N-(2-thiazolyl)-8-trifluoromethyl-3-quinoline-carboxamide melting at 240° C.

Analysis: $C_{30}H_{20}F_3N_3O_6S$; molecular weight=607.658.

|  | % C | % H | % N | % F | % S |
|---|---|---|---|---|---|
| Calculated: | 59.31 | 3.32 | 6.91 | 9.38 | 5.28 |
| Found: | 59.2 | 3.2 | 6.9 | 9.6 | 5.4 |

EXAMPLE 7

2-1,2-diacetyloxy-ethyl]-4-hydroxy-N-(2-thiazolyl)-8-trifluoromethyl-3-quinoline-carboxamide Using the procedure of Example 4, 2 g of the product of Example 2, 0.7 ml of acetic acid, 2.7 g of dicyclohexylcarboxiimide and 0.3 g of 4-dimethylamino-pyridine were reacted to obtain 0.9 g of raw product containing a little dicyclohexylurea. The impurity was removed by washing with tetrahydrofuran and the product was crystallized from dimethylformamide. The product was dissolved in tetrahydrofuran and an ethanolic solution of hydrogen chloride was added thereto and the product formed was crystallized from acetic acid to obtain 0.38 g of 2-1,2-diacetyloxy-ethyl]-4-hydroxy-N-(2-thiazolyl)-8-trifluoromethyl-3-quinoline carboxamide melting at 270° C.

Analysis: $C_{20}H_{16}F_3N_3O_6S$; molecular weight=483.432.

|  | % C | % H | % N | % F | % S |
|---|---|---|---|---|---|
| Calculated: | 49.69 | 3.34 | 8.69 | 11.79 | 6.63 |

-continued

|  | % C | % H | % N | % F | % S |
|---|---|---|---|---|---|
| Found: | 49.4 | 3.2 | 8.4 | 11.9 | 6.8 |

EXAMPLE 8

2-(2,2-dimethyl-1,3-dioxolan-4-yl)-4-hydroxy-N-(2-thiazolyl)-8-trifluoromethyl-3-quinoline-carboxamide A suspension of 3 g of the product of Example 2 in 80 ml of acetone was heated to reflux and 0.3 g of p-toluene sulfonic acid were added. The mixture was refluxed for 5 hours, was cooled to 20° C. and was vacuum filtered. The crystals were dried under reduced pressure and dissolved in 100 ml of tetrahydrofuran warmed to 40° C. The mixture was filtered and was concentrated to one half volume. The mixture was cooled to 20° C. and ether was added. The mixture was vacuum filtered and the cyrstals were washed with ether and dried to obtain 1.2 g of 2-(2,2-dimethyl-1,3-dioxolan-4-yl)-4-hydroxy-N-(2-thiazolyl)-8-trifluoromethyl-3-quinoline-carboxamide melting at 250° C.

Analysis $C_{19}H_{16}F_3N_3O_4S$; molecular weight=439.417.

|  | % C | % H | % N | % F | % S |
|---|---|---|---|---|---|
| Calculated: | 51.94 | 3.67 | 9.56 | 12.97 | 7.30 |
| Found: | 51.8 | 3.5 | 9.4 | 12.8 | 7.1 |

EXAMPLE 9

4-hydroxy-2-(1-hydroxy-2-methoxy-ethyl)-N-(2-thiazolyl)-7-chloro-3-quinoline-carboxamide Step A:
2-[(2-chloro-3-methoxy-1-oxo-propyl)-amino]-β-oxo-N-(2-thiazolyl -4-chloro-benzene-propanamide Using the procedure of Step A of Example 1, 2-(1-chloro-2-methoxy-ethyl)-7-choir-4H-3,1-benzoxazine-4-one melting at 82° C. [prepared by reacting 2-chloro-3-methoxy-propanoic acid and 2-amino-4-chloro-benzoic acid by the process of Step A of Example 12 of European patent No. 40,573] was reacted to obtain a 76% yield of 2-[(2-chloro-3-methoxy-1-oxo-propyl)-amino]- -oxon- 2-thiazolyl)-4-chloro-benzene-propanamide melting at 180° C.

Step B:
2-(1-chloro-2-methoxy-ethyl)-4-hydroxy-N-(2-thiazolyl)-7-chloro-3-quinoline carboxamide Using the procedure of Step B of Example 1, the product of Step A was reacted to obtain 2-(1-chloro-2-methoxy-ethyl)-4-hydroxy-N-(2-thiazolyl)-7-chloro-3-quinoline-carboxamide which was used without isolation for the next step.

Step C: 1,3-dihydro-3-methoxymethyl-1-(2-thiazolyl)-imino]6-chloro-furo[3,4-b]quinoline-9-ol Using the procedure of Step C of Example 1, the product of Step B was reacted at reflux for 24 hours in tetrahydrofuran to obtain a 65% yield of 1,3-dihydro-3-methoxymethyl-1-[(2-thiazolyl)-imino]-6-chloro-furo[3,4-b[quinoline-9-ol melting at
>270° C.

Step D:
4-hydroxy-2-(1-hydroxy-2-methoxy-ethyl)-N-(2-thiazolyl)7-chloro-3-quinoline-carboxamide Using the procedure of Step D of Example 1, the product of Step C was stirred with 6 N hydrochloric acid for 36 hours to obtain 4-hydroxy-2-(1-hydroxy-2-methoxy- ethyl)-N-(2-thiazolyl)-7-chloro-3-quinoline-carboxamide melting at >270° C.

EXAMPLE 10

2-(1,2-dihydroxyethyl)-4-hydroxy-N-(2-thiazol )-7-chloro-3-quinoline-carboxamide Using the procedure of Example 2, the product of Example 9 was reacted to obtain 2-(1,2-dihydroxyethyl)-4-hydroxy-N-(2-thiazolyl)-7-chloro-3-quinoline-carboxamide.

EXAMPLE 11

2-(1-acetyloxypropyl)-4-hydroxy-N-(2-thiazolyl)-8-trifluoromethyl-3quinoline-carboxamide A suspension of 1 g of 1,3-dihydro-3-ethyl-1-[2thiazolyl)-imino]-5-(trifluoromethyl)-furo-[3,4-b]-quinolin9-ol (product prepared in Belgian Patent No. 896,941) in 20 ml of acetic acid was refluxed for 90 minutes and the solution obtained was cooled and poured into 20 ml of water. After separating, washing and drying 926 mg of 2-(1-acetyloxypropyl)-4-hydroxy-N-(2-thiazolyl)-8-trifluoro methyl-3-quinoline-carboxamide were obtained which was purified in refluxing ethyl acetate and was then cooled and separated to obtain 712 mg of the said product melting at 245° C.

EXAMPLE 12

4-hydroxy-2-[1-(1-oxopropoxy)-propyl]-N-(2-thiazolyl)-8-(trifluoromethyl)-3-quinoline carboxamide A suspension of 3 g of 1,3-dihydro-3-ethyl-1-[(2thiazolyl)-imino]-5-(trifluoromethyl)-furo-[3,4-b]-quinolin-9-ol in 60 ml of propionic acid was held in a bath at 100°-110° C. for 2 hours and 50 minutes and the solution obtained was cooled and poured into 600 ml of water. After separating and washing with water, 2.5 g of product were obtained which was purified by crystallization from 40 ml of ethyl acetate. The crystals were cooled and recovered by filtration to obtain 1 7 g of 4-hydroxy-2-[1-(1-oxopropoxy)-propyl] -N-(2-thiazolyl)-8-(trifluoromethyl)-3-quinoline carboxamide melting at 216° C.

EXAMPLE 13

2-(1-acetyloxy-2-methylpropyl)-4-hydroxy-N-(2-thiazolyl)-8-trifluoro methyl-3-quinoline carboxamide

STEP A:
2-(1-chloro-2-methylpropyl)-8-(trifluoromethyl)-4H-3,1-benzoxazin-4-one 10.25 g of 2-amino-3-trifluoromethyl benzoic acid in 20 ml of toluene and 18.6 g of 2-chloro-3-methyl butanoyl chloride (prepared by J. Org. Chem., Vol. 40, p. 3420 (1975)) were mixed together, and the procedure of Example 10 of Belgian Patent No. 896,941 was followed for the preparation of 11.9 g of 2-(1-chloro-2-methylpropyl)-8 (trifluoromethyl)-4H-3,1-benzoxazin-4-one melting at 78°-80° C.

STEP B:
3-isopropyl-1,3-dihydro-1-(2-thiazolyl)-imino}-5-(trifluo methyl)-furo-[3,4-b-quinolin-9-ol 10.6 g of N-(2-thiazolyl)-acetamide, 325 ml of tetrahydrofuran and 106 ml of n-butyllithium in hexane titrating 1.4 M and 11.4 g of 2-(1-chloro-2-methylpropyl)-8-(trifluoromethyl)-4H-3, benzoxazin-4-one of Step A in solution in 80 ml of tetrahydrofuran were reacted by the procedure of Step A of Example 6 of Belgian Patent No. 896,941 to obtain 13.8 g of 2-[(2-chloro-1-oxo-3-methylbutyl)-amino]-β-oxo-N-(2-thiazolyl)-3-(trifluoromethyl)-benzene propanamide melting at 186° C.

11.65 g of the latter product in 200 ml of tetrahydro furan and 3.8 g of 4-dimethylaminopyridine were refluxed for 16 hours and the tetrahydrofuran was eliminated under reduced pressure 200 ml of water were added to the residue, and the pH was adjusted to 1-2 with N hydrochloric acid addition. After separating, washing wit water and drying under reduced pressure at 100° C. 10.2 g of 3-isopropyl-1,3-dihydro-1-(2-thiazolyl)-imino]-5-(trifluoromethyl)-furo-[3,4-b]-quinolin-9-ol melting at 246° to 248° C. were obtained.

STEP C:
2-(1-acetyloxy-2-methylpropyl)-4-hydroxy-N-(2-thiazolyl)-8trifluoromethyl-3-quinoline carboxamide 10 g of product of Step B in 200 ml of acetic acid we refluxed for 57 hours and the solution was allowed to return to ambient temperature. Then, 200 ml of water were added followed by filtration. The orange product was washed with water and then was dissolved in a mixture of 250 ml of ethyl acetate and 500 ml of tetrahydrofuran. The mixture was dried and 1 g of active carbon was added. After filtering and concentrating to dryness under reduced pressure, 8.3 g of residue were obtained which was crystallized from 240 ml of ethyl acetate. The crystals were filtered hot, cooled, separated, dried under reduced pressure at 40° C. for 16 hours; 5.3 g of expected product were obtained, melting at 242° C.

EXAMPLE 14
4-hydroxy-2-[2-methyl-1-(1-oxopropoxy)-propyl]-N-(2-thiazolyl)-8trifluoromethyl-3-quinoline carboxamide A suspension of 10 g of the compound of Step A of Example 13 in 200 ml of propionic acid was refluxed for 10 hours and then allowed to return to ambient temperature. 200 ml of wate were added and then, after filtering and washing with water, the residue was dissolved in a mixture of 300 ml of ethyl acetate and 500 ml of tetrahydrofuran After drying, filtering and concentrati to dryness under reduced pressure, 8.1 g of product were obtained which was crystallized from 90 ml of ethyl acetate. The crystals were filtered hot, separated, dried for 16 hours under reduced pressure at ambient temperature to obtain 5.5 g of 4-hydroxy-2-[2-methy-1-(1-oxopropoxy)-propyl]-N-(2-thiazolyl)-8-trifluoromethyl-3-quinoline carboxamide melting at 222° C.

EXAMPLE 15
4-hydroxy-2-[1-(1-oxopropoxy)-propyl]-N-(2-thiazolyl)-8-trifluoromethyl-3-quinoline carboxamide 1.24 g of dicyclohexylcarbodiimide were added to a suspension of 2 g of 4-hydroxy-2-(1-hydroxypropyl)-N-(2-thiazolyl)-8 trifluoromethyl-3-quinoline carboxamide [prepared as in Step C of Example 10 of Belgian Patent No. 896,941]and 0.4 ml of propionic acid in 20 ml of methylene chloride After stirring for 5 minutes, 0.30 g of 4-dimethylamino-pyridine were added and the mixture stood for an hour with stirring at ambient temperature The dicyclohexylurea formed was filtered off and the organic phase was washed with N hydrochloric acid, then with an aqueous solution of sodium bicarbonate, then with water, followed by drying and concentrating to dryness under reduced pressure The residue was taken up in 15 ml of ether, filtered, dried under reduced pressure to obtain 2.2 g of 4-hydroxy-2-[1-(1-oxopropoxy)-propyl]-N-(2-thiazolyl)-8-trifluoromethyl-3-quinoline carboxamide melting at 216° C. which was identical to that obtained in Example 2.

EXAMPLE 16
1-[4-hydroxy-3-[(2-thiazolylamino)-carbonyl]-8-(trifluoromethyl)-2quinolinyl]-propyl amino acetate dichlorohydride

STEP A:
[(1,1-dimethylethoxycarbonyl)-amino]-acetate of 1-[4-hydrox-3-[(2-thiazolylamino)-carbonyl]-8-(trifluoromethyl)-2-quinolinyl]propyl Using the procedure of Example 5, 12 g of 4-hydroxy-2(1-hydroxypropyl)-N-(2-thiazolyl)-8-trifluoromethyl-3-quinoline carboxamide and 5.3 g of N-tertbutoxycarbonyl glycine were reacted to obtain 15.8 g of [(1,1-dimethylethoxycarbonyl)-amino]-acetate of 1-[4-hydroxy]3-[(2-thiazolylamino}-carbonyl]-8-(trifluoromethyl)-2quinolinyl]-propyl melting at 196° C.

STEP B:
1-[4-hydroxy-3-[(2-thiazolylamino)-carbonyl]-8-(trifluoromethyl)-2-quinollinyl]-propylamino acetate dichlorohydride A mixture of 14 g of the product of Step A, 70 ml of methylene chloride and 42 ml of a 5.75N solution of ethanol in hydro chloric acid was stirred for 18 hours at ambient temperature and the precipitate is filtered, washed with methylene chloride, then with ether and dried under reduced pressure to obtain 13 g of crude product. The latter was dissolved in 125 ml of methanol and crystal lized by the addition of 170 ml of ethyl acetate. After separating, washing with ethyl acetate, and drying under reduced pressure, 8.4 g of 1-[4-hydroxy-3-[2-thiazolylamino)-carbonyl]-8-trifluoromethyl)-2quinolinyl]-propyl amino acetate dichlorohydride melting at 215° C. were obtained.

EXAMPLE 17
1-[4-hydroxy-3-[(2-thiazolylamino)-carbonyl]-8-trifluoromethyl)-2quinolinyl]-propyl butanoate Using the procedure of Example5, 8 g of 4-hydroxy-2(1-hydroxypropyl)-N-(2-thiazolyl)-8-trifluoromethyl-3-quinoline carboxamide and 2 ml of butyric acid were reacted to obtain 7.8 g of 1-[4-hydroxy 3-[(2-thiazolylamino)-carboxyl]-8-trifluoromethyl)-2quinolinyl]-propyl butanoate melting at 203° C.

EXAMPLE 18

1-[4-hydroxy-3-[(2-thiazolylamino)-carbonyl]-8-(trifluoromethyl)-2quinolinyl]-propyl-2,2-dimethylpropanoate Using the procedure of Example5, 5 g of 4-hydroxy-2(1-hydroxypropyl)-N-(2-thiazolyl)-8-trifluoromethyl-3-quinoline carboxamide and 1.4 g of pivalic acid were reacted to obtain 5.15 g of 1-[4-hydroxy-3-[(2-thiazolylamino)-carbonyl]-8-(trifluoromethyl) -2-quinolinyl]-propyl-2,2-dimethylpropanoate melting at 244° C.

EXAMPLE 19

1-[4-hydroxy-3-(2-thiazolylamino)-carbonyl]-8-(trifluoromethyl)-2quinolinyl]-propyl dodecanoate Using the procedure of Example 15, 5 g of 4-hydroxy-2(1-hydroxypropyl)-N-(2-thiazolyl)-8-trifluoromethyl-3-quinoline carboxamide and 2.8 g of lauric acid were reacted to obtain 6 g of 1-[4-hydroxy-3-(2-thiazolylamino)-carbonyl]-8-(trifluoromethyl)-2quinolinyl]-propyl dodecanoate melting at 158° C.

EXAMPLE 20

1-[4-hydroxy-3-[(2-thiazolylamino)-carbonyl]-8-(trifluoromethyl)-2quinolinyl]-propyl-3-pyridine carboxylate Using the procedure of Example 15, 5 g of 4-hydroxy-2(1-hydroxypropyl)-N-(2-thiazolyl)-8-trifluoromethyl-3-quinoline carboxamide and 1 68 g of nicotinic acid were reacted to obtain 4.75 g of 1-[4-hydroxy-3-[(2-thiazolylamino)-carbonyl]-8-(trifluoromethyl) -2-quinolinyl]-propyl-3-pyridine carboxylate melting at 200° C.

EXAMPLE 21

2-[1-(benzoyloxy)-propyl]-4-hydroxy-N-(2-thiazolyl)-8-(trifluoromethyl)-3-quinoline carboxamide Using the procedure of Example 15, 5 g of 4-hydroxy-2(1-hydroxypropyl)-N-(2-thiazolyl)-8-trifluoromethyl-3-quinoline carboxamide and 1.7 g of benzoic acid were reacted to obtain 4.65 g of 2-[1-(benzoyloxy)-propyl]-4-hydroxy-N-(2-thiazolyl)-8-(trifluoromethyl)-3-quinoline carboxamide melting at 230° C.

EXAMPLE 22

1-[4-hydroxy-3-[(2-thiazolylamino-carbonyl-8-trifluoromethyl-2quinolinyl]-propyl-3-phenyl-2-propenoate Using the procedure of Example 15, 5 g of 4-hydroxy-2(1-hydroxypropyl)-N-(2-thiazolyl)-8-trifluoromethyl-3-quinoline carboxamide and 2.05 g of cinnamic acid were reacted to obtain 4.65 g of 1-[4-hydroxy-3-[(2-thiazolylamino-carbonyl-8-trifluoromethyl-2quinolinyl]-propyl-3-phenyl-2-propenoate melting at 210° C.

EXAMPLE 23

1-[4-hydroxy-3-[(2-pyridinylamino)-carbonyl]-8-(trifluoromethyl)-2quinolinyl]-propyl propanoate

STEP A:

2-[(2-chloro-1-oxobutyl)-amino]-β-oxo-N-(2-pyridinyl)-3-trifluoromethyl benzene propanamide 314.3 ml of a 1.4M solution of n-butyllithium in hexane were added to a solution of 30 g of 2-acetylamino pyridine in 886 ml of tetrahydrofuran. After cooling to −70° C., a solution of 32 g of 2-(1-chloropropyl)-8-trifluoromethyl-4H-3,1-benzoxazine-4-or [prepared by the process of Example 10 of Belgian Patent No 896,941 in 230 ml of tetrahydrofuran was added and the solution was poured into 500 ml of 2N hydrochloric acid and 600 ml of water. The aqueou phase was extracted with ethyl acetate and the combined organic phases were dried and concentrated to dryness under reduced pressure. The residue was taken in ethyl ether, separated and dried to obtain 9.1 g of 2-[(2-chloro-1-oxobutyl)-amino]-β-oxo-N-(2-pyridinyl)-3-trifluoromethyl benzene propanamide melting at 137° C.

STEP B 1,3-dihydro-3-ethyl-2-[(2-pyridinyl)-amino]-5-trifluoromethyl furo [3,4-b]-quinolin-9-ol A mixture of 27 8 g of the product of Step A and 9.46 of 4-dimethylamino-pyridine in 500 ml of dioxane was refluxed for 90 minutes and after cooling, eliminating the solvent under reduced pressure, taking up the residue in 300 ml of ethyl ether and separating, the solid was dissolved in a 1-1 mixture of methylene chlorid and water. The aqueous phase was extracted with methylene chloride and the combined organic phases were dried and concentrated to dryne under reduced pressure After taking up the residue with ethyl ethe separating and drying the crystallized product, 14 4 g of 1,3-dihydr -3-ethyl-2-[(2-pyridinyl)-amino-5-trifluoromethyl furo [3,4-b]-quin lin-9-ol melting at 172° C. were obtained.

STEP C:

1-[4-hydroxy-3-[(2-pyridinylamino)-carbonyl]-8-(trifluorometh 2-quinolinyl]-propyl propanoate A mixture of 6 g of 1,3-dihydro-3-ethyl-2-[(2-pyridinyl)-amino]-5-trifluoromethyl furo [3,4-b]-quinolin-9-ol in 120 ml of propionic acid was refluxed for5 hours. After cooling and pouring into 150 ml of water, the precipitate was separated, washed with water and dissolved in 300 ml of ethyl acetate and 50 ml of tetrahydrofuran. The organic phase was washed, filtered over active carbon and concentrated to dryness under reduced pressure The residue was crystallized from ethyl acetate, and after separating and drying, 3.08 g of 1-[4-hydroxy-3-[(2-pyridinylamino)-carbonyl]-8-(trifluoromethyl)-2-quinolinyl-propyl propanoate melting at 204° C. were obtained.

EXAMPLE 24

1-4-hydroxy-3-[(2-pyridinyl)-aminocarbonyl]-8-trifluoromethyl-2quinolinyl]-2-methylpropyl acetate

STEP A:

2-[(2-chloro-3-methyl-1-oxobutyl)-amino]-β-oxo-N-(2-pyridinyl)-3-trifluoromethyl-benzene propanamide Using the procedure of Step A of Example 23, 10.16 g of 2-acetylaminopyridine, 106 ml of a hexane solution of n-butyllithium 1,4M) and 11.4 g of 2-(1-chloro-2-methylpropyl)-8-trifluoromethyl -4H-3,1-benzoxazin-4-one of Step A of example 3 were reacted to obtain 11.8 g of 2-[(2-chloro-3-methyl-1-oxobutyl)-amino]-β-oxo-N(2-pyridinyl)-3-trifluoromethyl-benzene propanamide melting at 136°–138° C.

STEP B
1,3-dihydro-3-(1-methylethyl)-1-(2-pyridinyl)imino]-5-tri fluoromethyl furo-3,4-b]-quinolin-9-ol 10.5 g of the product of Step A and 2.9 g of 4-dimet lamino-pyridine in 100 ml of tetrahydrofuran were refluxed for 7 hours 30 minutes and after cooling, the solvent was eliminated und reduced pressure. The residue was taken up in 100 ml. of water and 10 ml of acetone After separating, washing with water and drying at 70° C. under reduced pressure, 7.8 g of 1,3-dihydro-3-(1-methylethyl)-1-[(2-pyridinyl)-imino]-5-trifluoromethyl furo-[3,4-b]-quino lin-9-ol melting at 178°–180° C. were obtained

STEP C:
1-[4-hydroxy-3-[(2-pyridinyl)-aminocarbonyl]-8-trifluoromethy -2-quinolinyl]-2-methylpropyl acetate Using the procedure of Example 23, 6 g of 1,3-dihydro -3-(1-methylethyl)-1-[(2-pyridinyl)-imino]-5-trifluoromethyl furo[3,4-b]-quinolin-9-ol and 120 ml of acetic acid were reacted to obtain 3.5 g of 1-[4-hydroxy-3-[(2-pyridinyl)-aminocarbonyl-8-trifluoromethyl-2-quinolinyl]-2-methylpropyl acetate melting at 230° C.

EXAMPLE 25

1-[4-hydroxy-3-[(2-pyridinyl)-aminocarbonyl]-8-trifluoromethyl-2quinolinyl]-2-methyl-propyl propanoate Using the procedure of Example 5.9 g of 1,3-dihydro-3-(1-methylethyl)-1-[(2-pyridinyl)-imino]-5-trifluoromethyl furo-[3,4-b]-quinolin-9-ol of Example 14 and 120 ml of propionic acid were reacted to obtain 2.7 g of 1-[4-hydroxy-3-[(2-pyridinyl)-aminocarbonyl]-8-trifluoromethyl-2-quinolinyl]-1-methyl-propyl propanoate melting at 192° C.

EXAMPLE 26

4-hydroxy-2-[1-(1-oxopropoxy)-propyl]-N-(2-thiazolyl)-8-trifluoromethyl-3-quinoline carboxamide, isomer A STEP A: 1-[4-hydroxy-3-[(2-thiazolylamino)-carbonyl]-8-trifluromethyl-2-quinolinyl]-propyl-α-methoxy benzene acetate, isomers A and B 13.36 g of dicyclohexylcarbodiimide were added to a suspension of 12 g of R(-)methoxyphenylacetic acid, 28.7 g of 4hydroxy-2-(1-hydroxypropyl)-N-(2-thiazolyl)-8-trifluoromethyl-3-quinoline carboxamide [prepared as in Example 10 of Belgian patent No. 896,941]in 280 ml of methylene chloride and after stirring, 4.3 g of 4-dimethylamino-pyridine were added The mixture was stirred for 2 hours and 30 minutes and the dicyclohexylurea formed was filtered off. The organic phase was washed with N hydrochloric acid, then with a saturated aqueous solution of sodium bicarbonate, washed with water, dried and concentrated to dryness under reduced press to obtain 44.1 g of crude product. The latter was dissolved in 15 of methylene chloride and the insoluble matter was eliminated by filtration. Chromatography over silica and elution with ethyl acetate - hexane (1-1) yielded 15.18 g of isomer A melting at 172° C. and having a specific rotation of $[\alpha]_D = -26° \pm 3°$ (c=0.3%, methylene chloride) and 14.24 g of isomer B melting at 194° C. and having a specific rotation of $[\alpha]_D = -31° \pm 1°$ (c=1%, methylene chloride.

STEP B:
4-hydroxy-2-(1-hydroxypropyl)-N-(2-thiazolyl)-8-trifluoromethyl-3-quinoline carboxamide, isomer A 13.68 g of isomer A of Step A were added to 70 ml of butylamine and the mixture stood at ambient temperature for 24 hours After diluting with 500 ml of ethyl acetate, washing with 800 ml of 2N hydrochloric acid and then with water, drying and concentrating to drynss, 14.7 g of crude product were obtained After crystallization from ethyl acetate, 3.61 g of 4-hydroxy-2-(1-hydroxypropyl -N-(2-thiazolyl)-8-trifluoromethyl-3-quinoline carboxamide, isomer A melting at 180° C. were obtained $[\alpha]_D = -47° \pm 2°$ (c=0.5% in chloroform)

STEP C:
4-hydroxy-2-[1-(1-oxopropoxy)-propyl-N-(2-thiazolyl)-8-trifluoromethyl-3-quinoline carboxamide, isomer A Using the procedure of Example16 isomer A of 4-hydroxy-2-(1-hydroxypropyl)-N-(2-thiazolyl)-8-trifluoromethyl-3-quinoline carboxamide was reacted to obtain 4-hydroxy-2-[1-(1-oxopropoxy)-propyl]-N-(2-thiazolyl)-8-trifluoromethyl-3-quinoline carboxamide, isomer A melting at 187° C. and having a specific rotation of $[\alpha]_D = -9.5° \pm 1.5°$ (c=0.7% in acetone).

EXAMPLE 27

4-hydroxy-2-[1-(1-oxopropxy)-propyl]-N-(2-thiazolyl)-8-trifluoromethyl-3-quinoline carboxamide, isomer B

STEP A:
4-hydroxy-2-(1-hydroxypropyl)-N-(2-thiazolyl)-8-trifluoromethyl-3-quinoline carboxamide isomer B Using the procedure of Step B of Example 26, 12.14 g of isomer B of 1-[4-hydroxy-3-[(2-thiazolylamino carbonyl]-8-trifluoromethyl-2-quinolinyl]-propyl α-methoxy benzene acetate [prepared by the process of Step A of Example 16]were reacted to obtain 3.18 g of 4-hydroxy-2-(1-hydroxypropyl)-N-(2-thiazolyl)-8-trifluoromethyl-3-quinoline carboxamide isomer B melting at 180° C. and having a specific rotation of $[\alpha]_D = \pm 54° \pm 2.5°$ (c=0.5% in chloroform) and $[\alpha]_D = -51.5° \pm 2.5°$ (c=0 in acetone).

STEP B: 4-hydroxy-2-[1-(1-oxopropoxy)-propyl]-N-(2-thiazolyl)-8-trifluoromethyl-3-quinoline carboxamide, isomer B Using the procedure of Example 16, isomer B of 4-hydroxy-2[1-hydroxy-2-(1-hydroxypropyl)]-N-(2-thiazolyl)-8-trifluoromethyl-3-quinoline carboxamide, was reacted to obtain 4-hydroxy-2-[1-(1-oxopropoxy)-propyl]-N-(2-thiazolyl)-8-trifluoromethyl-3-quinoline carboxamide, isomer B melting at 187° C. and having a specific rotation of $[\alpha]_D = +8.5° \pm 1.5°$ (c=0.5% in acetone).

EXAMPLE 28

1-[4-hydroxy-3-{[(2-aminothiazolyl)-carbonyl]-8-trifluoromethyl2-quinolinyl]-propyl]1H-indole-2-carboxylate 5 g of 4-hydroxy-2-(1-hydroxypropyl)-N-(2-thiazolyl)-8-trifluoromethyl-3-quinolinecarboxamide [Example 10 of U.S. Pat. No. 4,486,438], 80 ml of methylene chloride and 2.43 g of 2-indole carboxylic acid were mixed together and then 3.11 g of dicyclohexylcarbodiimide and 0.77 g of 4-dimethylamino-pyridine were added all at once. The resulting precipitate was dissolved in methanol and the solution was evaporated to dryness to obtain 11 g of residue. The latter was chromatographed over silica and was eluted with a 9-1 methylene chloride-methanol mixture to obtain 8 g of product which were dissolved in 800 ml. of acetic acid. The solution was filtered and the product was iced and dried under reduced pressure at 100° C. to obtain 2 g of the expected product. The mother liquors were concentrated, iced and filtered. The product was dried under reduced pressure at 100° C. to obtain 4.25 g of the expected product melting at 260° C.

EXAMPLE 29

1-[4-hydroxy-3-[[(2-thiazolyl-amino]-carbonyl}-8-trifluoromethyl-2-quinolinyl-propyl] 2-propyl-5-thiazole-carboxylate Using the procedure of Example 28, 4 g of the product of Example 10 of U.S. Pat. No. 4,486,438, 50 ml of methylene chloride and 1.88 g of 5-isopropyl-2-thiazole-carboxylic acid were reacted with 2.48 g of dicyclohexylcarbodiimide and 0.61 g of 4-dimethylamino-pyridine to obtain 7 g of raw product. The latter was chromatographed over silica and was eluted with a 4-1 methylene chloride-ethyl acetate mixture to obtain 5 g of product which was crystallized from ethyl acetate to obtain 3.2 g of the expected product melting at 205°–210° C.

EXAMPLE 30

Tablets were prepared containing 50 mg of the product of Example 2 or Example 12 or Example 17 and sufficient excipient of lactose, talc, starch and magnesium stearate for a final tablet weight of 350 mg.

EXAMPLE 31

Tablets were prepared containing 50 mg of the product of step A of Example 27 (isomer B) and sufficient excipient of lactose, talc, starch and magnesium stearate for a final tablet weight of 350 mg.

PHARMACOLOGICAL STUDY

A. Anti-inflammatory activity chronic arthritis of adjuvant (preventative treatment)

The injection of adjuvant of "Freund" type into a hind paw causes in rats the rapid appearance of a primary inflammatory lesion in this paw and then after a latent period of 13 to 15 days, causes a secondary arthritis affecting in particular the other hind paw. The test was carried out on male rats aged from 42 to 50 days which received by intraplantar injection 0.1 ml of adjuvant of "Freund" type (suspension in vaseline oil of 6 mg per ml. of killed mycobacterium butyricum). The animals received the product studied orally from day 0 (day of the injection of the adjuvant) until the day before they were killed which occured on day 17. The arthritic control animals and normal control animals received only the vehicle. The assessment criteria of the activity of the substances studied were the increase in the volume of hind paws injected (primary and secondary inflammation) and not injected (secondary inflammation) in comparison with the average volume of paws corresponding to the normal controls. The $DA_{50}$ was determined, that is to say, the dose which reduced the increase in volume of the hind paws of the treated animals in comparison to those of the control animals by 50% and the results are reported in the following Table.

TABLE

| Product of Example | $DA_{50}$ in mg/kg |
|---|---|
| 1 | 2 |
| 2 | 0.7 |
| 3 | 3 |
| 4 | 1 |
| 5 | 5 |
| 12 | 0.8 |
| 17 | 1.3 |
| 16 | 1.0 |
| 28 | 2 |
| 29 | 2 |

B. Gastric ulceration effect

The test was done on female rats weighing 120 to 150 g on a water diet for 24 hours at the time of the treatment divided into random groupd. The products were administered orally and seven hours later, the animals were killed and their stomachs opened along the great curvature, washed in an isotonic solution of sodium chloride and spread apart by wiping with a cotton pad soaked in the same solution. The degree of ulcerous lesions, in number and in size, was estimated on a scale from 0 to 3 by two observers unware of the treatments. The notation 1 indicated the presence of an obvious ulcer or of several punctiform ulcers.

To take in account also the percentage of rats having ulcers (degree of ulceration greater than 0.5, notation attributed to a hyperemia or to Petechiae often encountered in a control which had fasted) an ulceration index was calculated for each group according to the formula $$\frac{\text{Degree of ulceration} \times \text{number of rats having an ulcer}}{\text{number of rats}} \times 100$$

The dose corresponding to an ulceration index of 100 or DU 100 was graphically determined (the maximum ulceration index is 300). The DU 100 was found to be greater than 300 mg/kg for the products of Examples 12 and 17.

C. Anti-inflammatory activity chronic arthritis of adjuvant (preventative treatment)

The injection of adjuvant of "Freund" type into a hind paw causes in rats the rapid appearance of a primary inflammatory lesion in this paw and then after a latent period of 13 to 15 days, causes a secondary arthritis affecting in particular the other hind paw. The test was carried out on male rats aged from 42 to 50 days which received by intraplantar injection 0.1 ml of adjuvant of "Freund" type (suspension in vaseline oil of 6 mg per ml. of killed mycobacterium butyricum). The animals received the product studied orally from day 0 (day of the injection of the adjuvant) until the day before they were killed which occured on day 17. The arthritic control animals and normal control animals received only the vehicle. The assessment criteria of the activity of the substances studied were the increase in the volume of hind paws injected (primary and secondary inflammation) and not injected (secondary inflammation) in comparison with the average volume of paws corresponding to the normal controls. The $DA_{50}$ was determined, that is to say the dose which reduced the increase in volume of the hind paws of the treated animals in comparison to those of the control animals by 50%. The product of Step A of Example 27 (B-isomer) had a DA$_{50}$ of 0.5 mg/kg.

Various modifications of the compounds and method of the invention may be made without departing from the spirit or scope thereof and it is to be understood that the invention is intended to be limited only as defined in the appended claims.

What we claim is:

1. A compound selected from the group consisting of a compound of the formula

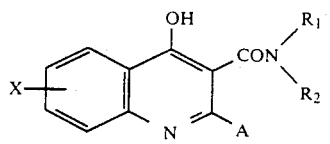

wherein X is in the 5-, 6-, 7- or 8-position and is selected from the group consisting of hydrogen, halogen, alkyl of 1 to 5 carbon atoms, alkoxy of 1 to 4 carbon atoms, —CF$_3$, —SCF$_3$ and —OCF$_3$, R$_1$ is selected from the group consisting of hydrogen and alkyl of 1 to 4 carbon atoms, R$_2$ is selected from the group consisting of thiazolyl, 4,5-dihydrothiazolyl, pyridinyl, oxazolyl, isoxazolyl, imidazolyl, pyrimidyl and tetrazolyl, all unsubstituted or substituted with alkyl of 1 to 4 carbon atoms and phenyl and phenyl substituted with at least one member of the group consisting of —OH, alkyl and alkoxy of 1 to 4 carbon atoms, —CF$_3$, —NO$_2$ and halogen, A is

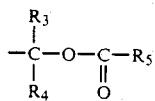

in which R$_3$ and R$_4$ are individually selected from the group consisting of hydrogen, alkyl of 1 to 4 carbon atoms, phenyl and naphthyl, R$_5$ is selected from the group consisting of pyridyl, indolyl, thienyl, oxazolyl, thiazolyl, pyrimidyl, benzo thienyl and benzothiazolyl unsubstituted or substituted with alkyl of 1 to 4 carbon atoms and their non-toxic, pharmaceutically acceptable salts with acids or bases.

2. A compound of claim 1 wherein X is in the 8-position.

3. A compound of claim 2 wherein X is —CF$_3$

4. A compound of claim 1 wherein X is in the 7-position.

5. A compound of claim 4 wherein X is chlorine.

6. A compound of claim 1 wherein R$_1$ is hydrogen.

7. A compound of claim 1 wherein R$_3$ is hydrogen.

8. A compound of claim 1 wherein R$_2$ is thiazolyl.

9. A compound of claim 1 wherein R$_4$ is ethyl.

10. A compound of claim 1 wherein R$_5$ is indolyl.

11. A compound of claim 1 wherein R$_5$ is thiazolyl optionally substituted with alkyl of 1 to 5 carbon atoms.

12. A compound of claim 1 selected from the group consisting of 1H-indole-carboxylate and 2-propyl-5-thiazole-carboxylate in racemic or optically active form and their non-toxic, pharmaceutically acceptable salts with acids and bases.

13. An analgesic and anti-inflammatory composition comprising an analgesically and anti-inflammatorily effective amount of at least one compound selected from the group consisting of a compound of claim 1 and an inert pharmaceutical carrier.

14. A composition of claim 13 wherein in the compound X is in the 8-position.

15. A composition of claim 14 wherein in the compound X is —CF$_3$.

16. A composition of claim 13 wherein in the compound X is in the 7-position.

17. A composition of claim 16 wherein in the compound X is chlorine.

18. A composition of claim 13 wherein in the compound R$_1$ is hydrogen.

19. A composition of claim 13 wherein in the compound R$_3$ is hydrogen.

20. A composition of claim 13 wherein in the compound R$_2$ is thiazolyl.

21. A composition of claim 13 wherein in the compound R$_4$ is ethyl.

22. A composition of claim 13 wherein in the compound R$_5$ is indolyl.

23. A composition of claim 13 wherein in the compound R$_5$ is thiazolyl optionally substituted with alkyl of 1 to 5 carbon atoms.

24. A composition of claim 13 wherein the active compound is selected from the group consisting of 1H-indole-carboxylate and 12-propyl-5-thiazole-carboxylate in racemic or optically active form and their non-toxic, pharmaceutically acceptable salts with acids and bases.

25. A method of relieving pain and inflammation in warm-blooded animals comprising administering to warm-blooded animals an analgesically and anti-inflammatorily effective amount of at least one compound selected from the group consisting of a compound of claim 1.

26. A method of claim 25 wherein in the active compound X is in the 8-position.

27. A method of claim 26 wherein in the active compound X is —CF$_3$.

28. A method of claim 25 wherein in the active compound X is in the 7-position.

29. A method of claim 28 wherein in the active compound X is chlorine.

30. A method of claim 25 wherein in the active compound R$_1$ is hydrogen.

31. A method of claim 25 wherein in the active compound R$_3$ is hydrogen.

32. A method of claim 25 wherein in the active compound R$_2$ is thiazolyl.

33. A method of claim 25 wherein in the active compound R$_4$ is ethyl.

34. A method of claim 25 wherein in the active compound R$_5$ is indolyl.

35. A method of claim 25 wherein in the active compound R$_5$ is thiazolyl optionally substituted with alkyl of 1 to 5 carbon atoms.

36. A method of claim 25 wherein the active compound is selected from the group consisting of 1111-indole-carboxylate and 12-propyl-5-thiazole-carboxylate in racemic or optically active form and their non-toxic, pharmaceutically acceptable salts with acids and bases.

* * * * *

UNITED STATES PATENT AND TRADEMARK OFFICE
CERTIFICATE OF CORRECTION

PATENT NO. : 4,988,708

DATED : Jan. 29, 1991

INVENTOR(S) : FRANCOIS CLEMENCE, ODILE LeMARTRET and FRANCOISE DELEVALLEE

It is certified that error appears in the above-identified patent and that said Letters Patent is hereby corrected as shown below:

| Col. | Line | | |
|---|---|---|---|
| 23 | Claim 12 | Left out --1-[4-hydroxy-3-{[(2-aminothiazolyl)-carbonyl]-8-trifluoromethyl-2-quinolinyl-propyl]-1H-indole-carboxylate and 1-[4-hydroxy-3-[(2-thiazolyl)-amino]-carboxyl-8-trifluoromethyl-2-quinolinyl-propyl] | |
| | | and delete "1H-indole-carboxylate and" | |
| 24 | Claim 24 | same as above Claim 12 | |
| | | delete "1H-carboxylate and 12-propyl" | |
| 24 | Claim 36 | delete "1111-indole-carboxylate and 12-propyl" and insert the same as Claim 12 and 24 | |

Signed and Sealed this

First Day of September, 1992

Attest:

DOUGLAS B. COMER

*Attesting Officer*  *Acting Commissioner of Patents and Trademarks*